(12) United States Patent
Weidner

(10) Patent No.: US 6,482,421 B2
(45) Date of Patent: Nov. 19, 2002

(54) PHARMACEUTICALS, DIETARY SUPPLEMENTS AND COSMETIC COMPOSITIONS, AND THE USE OF CERTAIN MIXTURES FOR PREPARING A MEDICAMENT OR A DIETARY SUPPLEMENT FOR THE TREATMENT OR PREVENTION OF INFLAMMATION, HYPERSENSITIVITY REACTIONS OR PAIN

(75) Inventor: Morten Sloth Weidner, Virum (DK)

(73) Assignee: Eurovita A/S, Karslunde (DK)

( * ) Notice: Subject to any disclaimer, the term of this patent is extended or adjusted under 35 U.S.C. 154(b) by 0 days.

(21) Appl. No.: 09/945,256

(22) Filed: Aug. 31, 2001

(65) Prior Publication Data

US 2002/0051800 A1 May 2, 2002

Related U.S. Application Data

(63) Continuation of application No. PCT/DK00/00087, filed on Mar. 2, 2000.

(30) Foreign Application Priority Data

Mar. 3, 1999 (DK) .......................... 1999 00293

(51) Int. Cl.[7] .......................... A61K 7/02; A61K 31/74; A61K 47/12
(52) U.S. Cl. ...................... 424/401; 424/78.03; 424/439
(58) Field of Search .................. 424/401, 439, 424/78.03

(56) References Cited

FOREIGN PATENT DOCUMENTS

| JP | 44008561 B | 10/1966 |
|----|------------|---------|
| JP | 1180822 | 7/1989 |
| JP | 7267856 | 10/1995 |
| WO | 96/31457 | 10/1996 |
| WO | 98/06276 | 2/1998 |

OTHER PUBLICATIONS

Parveen Kumar & Michael Clark, "Clinical Medicine" 3rd Edition, p. 147–150, 1994, Bailliere Tindall, London.

K.C. Srivastava and T. Mustafa, "Ginger (Zingiber officinale) and Rheumatic Disorders", Med. Hypotheses, May 1989, 29(1): 25–8.

K.C. Srivastave and T. Mustafa, "Ginger (Zingiber officinale) and Rheumatic Disorders", Med. Hypotheses, Dec. 1992, 39(4): 342–8.

F. Kiuchi, et al., "Inhibition of Prostaglandin and Leukotriene Biosynthesis by Gingerols and Diarylheptanoids". Chem. Phar. Bull., Tokyo, Feb. 1992 40(2): 387–91.

J.N. Sharma, et al., "Suppressive Effects of Eugenol and Ginger Oil on Arthritic Rats", Pharmacology 1994; 49: 314–18.

*Primary Examiner*—Carlos Azpuru
(74) *Attorney, Agent, or Firm*—Darby & Darby

(57) ABSTRACT

The present invention relates to mixtures comprising at least one the fatty acids eicosapentaenoic acid (20:5n3) and docosahexaenoic acid (22:6n3) and the plant *Zingiber officinale* Roscoe or parts thereof or an extract or a component thereof as novel pharmaceuticals, dietary supplements or cosmetic compositions containing such mixtures, and to the use of such mixtures for preparing a medicament or a dietary supplement for the suppression of hypersensitivity and/or inflammatory reaction.

3 Claims, No Drawings

PHARMACEUTICALS, DIETARY SUPPLEMENTS AND COSMETIC COMPOSITIONS, AND THE USE OF CERTAIN MIXTURES FOR PREPARING A MEDICAMENT OR A DIETARY SUPPLEMENT FOR THE TREATMENT OR PREVENTION OF INFLAMMATION, HYPERSENSITIVITY REACTIONS OR PAIN

This is a continuation of international application Ser. No. PCT/DK00/00087, filed Mar. 2, 2000, the entire disclosure of which is hereby incorporated by reference, which was published in English as WO 00/51576 and claims the benefit of Danish patent application No. PA 1999 00293, filed Mar. 3, 1999.

Novel pharmaceuticals. dietary supplements and cosmetic compositions, and the use of certain mixtures for preparing a medicament or a dietary supplement for the treatment or prevention of inflammation, hypersensitivity reactions or pain.

FIELD OF THE INVENTION

The present invention relates to mixtures comprising at least one of the fatty acids eicosapentaenoic acid (20:5n3) and docosahexaenoic acid (22.6n3) and the plant *Zingiber officinale* Roscoe or parts thereof or an extract or a component thereof.

More specifically, the invention relates to novel pharmaceuticals, dietary supplements or cosmetic compositions containing such mixtures, and to the use of such mixtures for preparing a medicament or a dietary supplement for the suppression of hypersensitivity and/or inflammatory reaction.

BACKGROUND OF THE INVENTION

Hypersensitivity is defined as a state of altered reactivity in which the body reacts with an exaggerated immune response to a substance (antigen). Hypersensitivity may be caused by exogenous or endogenous antigens.

Hypersensitivity reactions underlie a large number of diseases. Among these, allergic and autoimmune conditions are of great importance. A classification of hypersensitivity diseases is given in the textbook Clinical Medicine (Kumar, P. and Clark, M.: "Clinical Medicine", 3rd edition, p. 147–150, 1994, Bailliere Tindall, London).

Type I hypersensitivity reactions (IgE mediated allergic reactions) are caused by allergens (specific exogenous antigens), e.g. pollen, house dust, animal dandruff, moulds, etc. Allergic diseases in which type I reactions play a significant role include asthma, eczema (atopic dermatitis), urticaria, allergic rhinitis and anaphylaxis.

Type II hypersensitivity reactions are caused by cell surface or tissue bound antibodies (IgG and IgM) and play a significant role in the pathogenesis of myasthenia gravis, Good-pasture's syndrome and Addisonian pernicious anaemia.

Type III hypersensitivity reactions (immune complex) are caused by autoantigens or exogenous antigens, such as certain bacteria, fungi and parasite. Diseases in which type III hypersensitivity reactions play a significant role include lupus erythematosus, rheumatoid arthritis and glomerulonephritis.

Type IV hypersensitivity reactions (delayed) are caused by cell or tissue bound antigens. This type of hypersensitivity plays a significant role in a number of conditions, e.g. graft-versus-host disease, leprosy, contact dermatitis and reactions due to insect bites.

A number of drug classes are available for the treatment of hypersensitivity reactions. Some of these are applied systemically and some are applied topically.

The corticosteroids are among the most widely used drugs for the treatment of hyper-sensitivity diseases. Corticosteroids primarily exert their pharmacological action by non-selectively inhibiting the function and proliferation of different classes of immune cells resulting in suppression of hyper-sensitivity reactions. Unfortunately the corticosteroids are associated with a number of serious side effects, e.g. immuno-suppression, osteoporosis and skin atrophy (when applied topically)

*Zingiber officinale* Roscoe (family Zingiberacea), commonly known as ginger, is an erect perennial herb with thick tuberous rhizomes (underground stems) from which the aerial stem grows about 1 m high. *Zingiber officinale* Roscoe is native to Southern Asia, and is extensively cultivated in the tropics, e.g. India, China, Jamaica, Haiti and Nigeria.

Ginger or ginger volatile oil is widely used as a flavour ingredient in the food industry.

Due to the extensive use of *Zingiber officinale* Roscoe in the food industry, it has been subject to some chemical investigations.

The ginger rhizome contains a volatile oil which can be obtained by steam distillation. The chemical composition of ginger oil depends on its geographic origin. Ginger volatile oil generally contains the sesquiterpenes zingiberene and bisabolene as its major components. Other sesquiterpenes and sesquiterpene alcohols present include ar-curcumene, $\beta$-sesquiphelandrene, sesquithujene, $\beta$-bisabolone, (E)-$\alpha$-farnesene, zingiberol, zingiberenol, cis-sesquisabinene hydrate, and cis- and trans-sesquiphellandrol. It also contains monoterpenes such as camphor, $\beta$-phellandrene, geranial, neral, linalool, camphene and d-borneol.

*Zingiber officinale* Roscoe contains a number of phenolic compounds, most of which have a characteristic hydroxy-methoxy-phenyl moiety. These compounds are responsible for the pungency of ginger. The quantitatively dominating group of these phenolic compounds are the gingerols. The gingerols form a homologous series, 2-gingerol, 4-gingerol, 6-gingerol, 8-gingerol, 10-gingerol, 12-gingerol and 14-gingerol. The quantitatively dominating of these is 6-gingerol. Another group are the shogaols which are dehydration products of gingerols. The shogaols form a similar homologous series. Other similar compounds present are zingerone, 6-gingerdiol, gingerdione, gingerenones A-C, isogingerenone B, etc.

*Zingiber officinale* Roscoe has been used in the traditional medicine in China and in the Indian subcontinent for more than 2500 years. The Chinese prescribe fresh or dried ginger for the relief of a number of conditions, e.g. gastrointestinal disturbances, colds, inflammations, headaches and as an antiemetic for the prevention of seasickness.

The traditional use of *Zingiber officinale* Roscoe is limited to consumption of the ginger rhizome in a fresh or dried state. Obtaining an effect based on the traditional use requires high doses of the rhizome (Srivastava K C et al., Med. Hypotheses. May; 29, 1989 (1): 25–8 and Shrivastava K C et al, Med. Hypothesis Dec.; 39, 1992 (4): 342–8).

An inhibiting effect on the formation of pro-inflammatory eicosanoids has been established in vitro for some components of *Zingiber officinale* Roscoe (Kiuchi F, et al, Chem. Pharm. Bull. Tokyo. 1992 Feb; 40(2): 387–91). Furthermore an inhibiting effect of ginger oil on adjuvant arthritis in the rat has been established in vivo (Sharma J N et al, Pharmacology 1994;49: 314–18). Despite these findings, the pharmacological effects of *Zingiber officinale* Roscoe upon administration to humans are mild and only of limited clinical relevance.

The arachidonic acid (AA) metabolism plays an essential role in hyper-sensitivity reactions because AA is converted by the enzyme cyclooxygenase into pro-inflammatory prostaglandins and by the enzyme 5-lipoxygenase into proinflammatory leukotrienes. The prostaglandins and leukotrienes are commonly termed eicosanoids. The modulation of the AA metabolism is a well established pharmacological strategy in relation to the treatment of hyper-sensitivity reactions.

Marine oils, especially fish oils, contain relatively high concentrations of the fatty acids eicosapentaenoic acid (20:5n3) and docosahexaenoic acid (22:6n3). These fatty acids have been shown to reduce inflammatory reactions because they can replace AA in the AA metabolism. The eicosanoids formed by the metabolism of eicosapentaenoic acid (20:5n3) and docosahexaenoic acid (22:6n3) have insignificant pro-inflammatory effects or even antiinflammatory effects.

The drawback in relation to the therapeutic use of eicosapentaenoic acid (20:5n3) and docosahexaenoic acid (22:6n3) is that they are only mildly antiinflammatory and need to be administered for longer periods before a clinical effect can be observed.

SUMMARY OF THE INVENTION

It has been found by the present inventor that a combination of:

a) eicosapentaenoic acid (20:5n3) and/or docosahexaenoic acid (22:6n3), and b) *Zingiber officinale* Roscoe or parts thereof or an extract or component thereof;

significantly suppresses hyper-sensitivity reactions, and that such a combination is far superior to any of its components when they are used alone.

To the inventor's best knowledge, it is disclosed nowhere in the literature to use a combination of:

a) eicosapentaenoic acid (20:5n3) and/or docosahexaenoic acid (22:6n3), and b) *Zingiber officinale* Roscoe or parts thereof or an extract or component thereof; as active ingredients in pharmaceuticals, dietary supplements or cosmetics.

As mentioned above the therapeutic effect of *Zingiber officinale* Roscoe is derived from the ability of certain components to inhibit the generation of eicosanoids through a direct inhibition of cyclooxygenase and 5-lipoxygenase. The therapeutic efficacy of *Zingiber officinale* Roscoe is limited strongly by the fact that its pharmacologically active components are only mild inhibitors of eicosanoid generation.

Furthermore the fatty acids eicosapentaenoic acid (20:5n3) and/or docosahexaenoic acid (22:6n3) have a limited therapeutic efficacy, simply because they are only able to replace a limited fraction of the cellular pool of arachidonic acid after oral administration.

Surprisingly the present inventor has found that a combination of:

a) eicosapentaenoic acid (20:5n3) and/or docosahexaenoic acid (22:6n3), and b) *Zingiber officinale* Roscoe or parts thereof or an extract or component thereof; provides a synergistic effect in the treatment of hyper-sensitivity reactions, probably because both substances modulate the arachidonic acid metabolism, but at different levels.

According to the present invention eicosapentaenoic acid (20:5n3) and/or docosahexaenoic acid (22:6n3) can be used in the form of free fatty acids or esters of any mono- or polyvalent alcohol. Preferably the fatty acids may be used in the form of mono-, di- or triglycerides which can be derived from a number of natural sources, especially marine sources, such as fish in the form of fish oils.

According to the present invention *Zingiber officinale* Roscoe or parts thereof or an extract or component thereof may be used in any form, such as powdered plant material, extracts, concentrates or distillates or in the form of purified components of the plant, such as 2-gingerol, 4-gingerol, 6-gingerol, 8-gingerol, 10-gingerol, 12-gingerol, 14-gingerol, 2-shogaol, 4-shogaol, 6-shogaol, 8-shogaol, 10-shogaol, 12-shogaol, 14-shogaol, zingerone, 6-gingerdiol, gingerdione, gingerenones, isogingerenones, zingiberene, bisabolene, ar-curcumene, β-sesquiphelandrene, sesquithujene, β-bisabolone, (E)-α-farnesene, zingiberol, zingiberenol, cis-sesquisabinene hydrate, cis-sesquiphellandrol, trans-sesquiphellandrol and β-phellandrene, or any mixture of any of these substances.

The broad definition of *Zingiber officinale* Roscoe or parts thereof or an extract or component thereof is explained by the fact that the pharmacological effects of *Zingiber officinale* Roscoe is caused by a broad spectrum of pharmacologically active compounds, even though, of course, some substances are preferred.

Compared to existing therapeutic agents, such as corticosteroids or non-steroidal-antiinflammatory drugs, the pharmaceutical compositions, dietary supplements and cosmetic compositions according to the present invention have the advantage of not being likely to be associated with any serious side effects, as eicosapentaenoic acid (20:5n3), docosahexaenoic acid (22:6n3), and *Zingiber officinale* Roscoe are non-toxic and well tolerated by the organism in the pharmacologically relevant doses.

Due to the pharmacological effects mentioned above, probably caused by modulation of the arachidonic acid metabolism, the pharmaceutical compositions, dietary supplements and cosmetic compositions according to the invention can be employed for the following therapeutic applications.

Immunomodulation.

Treatment or prevention of hyper-sensitivity diseases.

Treatment or prevention of IgE mediated allergic reactions and conditions.

Treatment or prevention of autoimmune disorders.

Alleviation of pain.

Accordingly, the present invention provides a pharmaceutical, a dietary supplement or a cosmetic composition, comprising:

a) eicosapentaenoic acid (20:5n3) and/or docosahexaenoic acid (22:6n3), b) *Zingiber officinale* Roscoe or parts thereof or an extract or component thereof, and c) a pharmaceutically and/or cosmetically acceptable vehicle.

Furthermore, the present invention provides the use of a mixture comprising:

a) eicosapentaenoic acid (20:5n3) and/or docosahexaenoic acid (22:6n3), b) *Zingiber officinale* Roscoe or parts thereof or an extract or component thereof, and c) a pharmaceutically acceptable vehicle; for preparing a medicament for immunomodulation, for the suppression of hyper-sensitivity reactions, such as IgE mediated allergic reactions and autoimmune reactions, and for the alleviation of pain.

Thus, according to the invention a mixture comprising:

a) eicosapentaenoic acid (20:5n3) and/or docosahexaenoic acid (22:6n3), b) *Zingiber officinale* Roscoe or parts thereof or an extract or component thereof, and c) a pharmaceutically acceptable vehicle; can be used in a method for the treatment or prevention of a hyper-sensitivity disease in an individual, said method comprising administering said mixture to said individual; and the invention comprises the use of said mixture for preparing a medicament for the treatment or prevention of hyper-sensitivity diseases.

Also, according to the invention a mixture comprising:
a) eicosapentaenoic acid (20:5n3) and/or docosahexaenoic acid (22:6n3),
b) *Zingiber officinale* Roscoe or parts thereof or an extract or component thereof, and
c) a pharmaceutically acceptable vehicle; can be used in a method for the treatment or prevention of an autoimmune disorder in an individual, said method comprising administering said mixture to said individual; and the invention comprises the use of said mixture for preparing a medicament for the treatment or prevention of autoimmune disorders.

Further, according to the invention a mixture comprising:
a) eicosapentaenoic acid (20:5n3) and/or docosahexaenoic acid (22:6n3),
b) *Zingiber officinale* Roscoe or parts thereof or an extract or component thereof, and
c) a pharmaceutically acceptable vehicle; can be used in a method for the treatment or prevention of an IgE mediated allergic reaction or condition in an individual, said method comprising administering said mixture to said individual; and the invention comprises the use of said mixture for preparing a medicament for the treatment or prevention of IgE mediated allergic reactions and conditions.

Also, according to the invention a mixture comprising:
a) eicosapentaenoic acid (20:5n3) and/or docosahexaenoic acid (22:6n3),
b) *Zingiber officinale* Roscoe or parts thereof or an extract or component thereof, and
c) a pharmaceutically acceptable vehicle; can be used in a method for the alleviation of pain in an individual, said method comprising administering said mixture to said individual; and the invention comprises the use of said mixture for preparing a medicament for the alleviation of pain.

DETAILED DESCRIPTION OF THE INVENTION

Surprisingly it has been found that a mixture comprising:
a) eicosapentaenoic acid (20:5n3) and/or docosahexaenoic acid (22:6n3),
b) *Zingiber officinale* Roscoe or parts thereof or an extract or component thereof, and
c) a pharmaceutically acceptable vehicle; exerts pharmacological actions relevant to the therapeutic treatment of conditions associated with hyper-sensitivity reactions and pain.

More specifically, the above mentioned mixtures provide the following pharmacological effects upon administration to the living organism:

Immunomodulation.

Suppression of hyper sensitivity reactions.

Suppression of IgE mediated allergic reactions.

Suppression of autoimmune reactions.

Reduction of pain.

The present invention provides a pharmaceutical, a dietary supplement or a cosmetic composition, comprising:
a) eicosapentaenoic acid (20:5n3) and/or docosahexaenoic acid (22:6n3),
b) *Zingiber officinale* Roscoe or parts thereof or an extract or component thereof, and
c) a pharmaceutically and/or cosmetically acceptable vehicle.

The weight percentage (w/w) of eicosapentaenoic acid (20:5n3) and/or docosahexaenoic acid (22:6n3) in the composition is typically at least 0.1%, such as at least 0.2%, e.g. at least 0.3%, at least 0.5%, at least 0.75%, at least 1.0%, at least 1.5%, such as at least 2.0%, e.g. at least 2.5%, at least 3.0%, at least 4.0%, at least 5.0%, at least 10.0%, such as at least 20.0%, e.g. at least 30.0%, at least 40.0%, at least 50.0%, at least 60.0%, at least 70.0%, at least 80.0%, at least 90.0%, such as at least 95.0%, e.g. at least 96.0%, at least 97.0%, at least 98.0%, at least 99.0%.

The weight percentage (w/w) of *Zingiber officinale* Roscoe or parts thereof or an extract or component thereof in the composition is typically at least 0.1%, such as at least 0.2%, e.g. at least 0.3%, at least 0.5%, at least 0.75%, at least 1.0%, at least 1.5%, such as at least 2.0%, e.g. at least 2.5%, at least 3.0%, at least 4.0%, at least 5.0%, at least 10.0%, such as at least 20.0%, e.g. at least 30.0%, at least 40.0%, at least 50.0%, at least 60.0%, at least 70.0%, at least 80.0%, at least 90.0%, such as at least 95.0%, e.g. at least 96.0%, at least 97.0%, at least 98.0%, at least 99.0%.

According to the present invention eicosapentaenoic acid (20:5n3) and/or docosahexaenoic acid (22:6n3) can be used in the form of free fatty acids or esters of any mono- or polyvalent alcohol. Preferably the fatty acids may be used in the form of mono-, di- or tri-glycerides which can be derived from a number of natural sources, especially marine sources, such as fish in the form of fish oils.

According to the present invention *Zingiber officinale* Roscoe or parts thereof or an extract or component thereof may be used in any form, such as powdered plant material, extracts, concentrates or distillates or in the form of purified components of the plant, such as 2-gingerol, 4-gingerol, 6-gingerol, 8-gingerol, 10-gingerol, 12-gingerol, 14-gingerol, 2-shogaol, 4-shogaol, 6-shogaol, 8-shogaol, 10-shogaol, 12-shogaol, 14-shogaol, zingerone, 6-gingerdiol, gingerdione, gingerenones, isogingerenones, zingiberene, bisabolene, ar-curcumene, β-sesquiphelandrene, sesquithujene, β-bisabolone, (E)-α-famesene, zingiberol, zingiberenol, cis-sesquisabinene hydrate, cis-sesquiphellandrol, trans-sesquiphellandrol and β-phellandrene.

In a preferred embodiment of the invention the part of *Zingiber officinale* Roscoe is an extract. Extracts according to the invention can i.a. be obtained by extraction or distillation (e.g. hydro, steam or vacuum distillation) of fresh or dried *Zingiber officinale* Roscoe or parts thereof, preferably the rhizome. Extraction may be performed with a number of different organic solvents, such as water miscible solvents, and mixtures thereof with water. The extraction can also be performed with water immiscible solvents, such as alkanes. The extraction can be performed hot or cold by the employment of any extraction technology e.g. maceration, percolation or supercritical extraction.

The preferred extraction solvents are pentane, hexane, heptane, acetone, methyl ethyl ketone, ethyl acetate, lower alkanols having 1 to 4 carbon atoms and mixtures thereof with water. The preferred extraction temperature is close to the boiling point of the employed solvent due to extraction efficacy, but lower temperatures are also applicable making necessary a longer period of extraction. Supercritical extraction (e.g. performed with $CO_2$) is also a preferred mode of extraction.

A "dietary supplement" is defined according to the U.S. Food and Drug Administration in the Dietary Supplement Health and Education Act of 1994 (DSHEA).

The DSHEA gives the following formal definition of a "dietary supplement":

"A dietary supplement:
is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract, or combinations of these things.

is intended for ingestion in pill, capsule, tablet, or liquid form."

Similar definitions exist in other parts of the world, e.g. in Europe, in the present context, the definition is as defined above. Different denominations concerning "dietary supplements" are used around the world, such as "food supplements", "neutraceuticals", "functional foods" or simply "foods". In the present context the term "dietary supplement" covers any such denomination or definition.

The above mentioned pharmacological actions provide part of the rationale for the following therapeutic applications of a mixture comprising.

a) eicosapentaenoic acid (20:5n3) and/or docosahexaenoic acid (22:6n3), b) *Zingiber officinale* Roscoe or parts thereof or an extract or component thereof, and c) a pharmaceutically acceptable vehicle:

A method for the treatment or prevention of hyper-sensitivity disease characterised by the administration of the above mentioned mixture. The therapeutic action may be relevant to all known diseases associated with hyper-sensitivity reactions. Autoimmune disorders and IgE mediated allergic conditions are described below in more detail. Besides these specific therapeutic areas, the action of the above mentioned mixture is relevant to all known conditions and diseases associated with hyper-sensitivity reaction, and the following examples are not limiting with respect to this: infections (viral, bacterial, fungal, parasitic, etc.), cold and flu, contact dermatitis, insect bites, allergic vasculitis, postoperative reactions, transplantation rejection (graft-versus-host disease), etc.

A method for the treatment or prevention of autoimmune disorders characterised by the administration of the above mentioned mixture. The applicant puts forward the hypothesis that the therapeutic action is due to the immunomodulating and suppressing effect on hyper-sensitivity reactions of the above mentioned mixture. The therapeutic action may be relevant to all known autoimmune disorders and the following examples are not limiting with respect to this: Autoimmune hepatitis, Primary biliary cirrhosis, Primary sclerosing cholangitis, Autoimmune hemolytic anemias, Grave's disease, Myasthenia gravis, Type 1 Diabetes Mellitus, Inflammatory myopathies, Multiple sclerosis, Hashimoto's thyreoiditis, Autoimmune adrenalitis, Crohn's Disease, Ulcerative Colitis, Glomerulonephritis, Progressive Systemic Sclerosis (Scleroderma), Sjögren's Disease, Lupus Erythematosus, Primary vasculitis, Rheumatoid Arthritis, Juvenile Arthritis, Mixed Connective Tissue Disease, Psoriasis, Pemfigus, Pemfigoid, Dermatitis Herpetiformis, etc.

A method for the treatment or prevention of an IgE mediated allergic reaction or condition characterised by the administration of the above mentioned mixture. The applicant puts forward the hypothesis that the therapeutic action is due to the suppressing effect on hyper-sensitivity reaction of the above mentioned mixture. The therapeutic action may be relevant to all known IgE mediated allergic reactions and conditions, and the following examples are not limiting with respect to this: asthma, eczema (e.g. atopic dermatitis), urticaria. allergic rhinitis, anaphylaxis, etc.

A method for the treatment or prevention of any condition associated with pain characterised by the administration of the above mentioned mixture. The applicant puts forward the hypothesis that the therapeutic action is related to immunomodulation, possibly to a suppressing effect on hyper-sensitivity reactions.

According to the invention the above mentioned mixture can be combined with any other active ingredient to potentiate the therapeutic action.

Vehicles other than water that can be used in compositions can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

solvents, such as water, methylene chloride, isopropanol, castor oil, ethylene glycol monoethyl ether, diethylene glycol monobutyl ether, diethylene glycol monoethyl ether, dimethyl sulfoxide, tetrahydrofuran, vegetable and animal oils, glycerol, ethanol, propanol, propylene glycol, and other glycols or alcohols, fixed oils;

humectants or moistening agents, such as glycerin, sorbitol, sodium 2-pyrrolidone-5-carboxylate, soluble collagen, dibutyl phthalate, gelatin;

powders, such as chalk, talc, kaolin, starch and derivatives thereof, gums, colloidal silicon dioxide, sodium polyacrylate, chemically modified magnesium aluminium silicate, hydrated aluminium silicate, carboxyvinyl polymer, sodium carboxymethyl cellulose, ethylene glycol monostearate;

gelling or swelling agents, such as pectin, gelatin and derivatives thereof, cellulose derivatives such as methyl cellulose, carboxymethyl cellulose or oxidised cellulose, cellulose gum, guar gum, acacia gum, karaya gum, tragacanth gum, bentonite, agar, alginates, carbomer, gelatine, bladderwrack, ceratonia, dextran and derivatives thereof, ghatti gum, hectorite, ispaghula husk, xanthan gum;

polymers, such as polylactic acid or polyglycolic acid polymers or copolymers thereof, paraffin, polyethylene, polyethylene oxide, polyethylene glycol, polypropylene glycol, polyvinylpyrrolidone;

surfactants, such as non-ionic surfactants, e.g. glycol and glycerol esters, macrogol ethers and esters, sugar ethers and esters, such as sorbitan esters, ionic surfactants, such as amine soaps, metallic soaps, sulfated fatty alcohols, alkyl ether sulfates, sulfated oils, and ampholytic surfactants and lecitins;

buffering agents, such as sodium, potassium, aluminium, magnesium or calcium salts (such as the chloride, carbonate, bicarbonate, citrate, gluconate, lactate, acetate, gluceptate or tartrate).

Furthermore, it is obvious that in the use according to the invention for preparing medicaments, dietary supplements or cosmetics, the above mentioned mixture may be mixed with additives such as surfactants, solvents, thickeners, stabilisers, preservatives, antioxidants, flavours, etc. to obtain a desirable product formulation. Similarly, a pharmaceutical, dietary supplement or cosmetic composition according to the invention may further contain such additives. There are no limitations on the route of administration or dosage form of the formulation, and the following examples are not limiting with respect to this: tablets, capsules, lozenges, chewing gum, fluids, granulates, gels, ointments, emulsions (e.g. creams and lotions), sprays (e.g. aerosol), inhalants, eye drops, etc. Optionally, the composition may also contain surfactants such as bile salts, polyoxyethylene-sorbitan-fatty acid esters or polyalcohol mixed chain-length fatty acid esters for improving dispersibility of the composition in the digestive fluids leading to improved bioavailability or for obtaining the final dosage form of the composition.

In preferred embodiments of the present invention the described pharmaceutical, dietary supplement or cosmetic composition is used in mammals, such as a human.

EXAMPLES

Example 1

A pharmaceutical composition or dietary supplement according to the invention was prepared as follows:

100 g of dried rhizome of *Zingiber officinale* Roscoe was percolated with 1000 ml of acetone for 24 hours. Thereafter the extract was filtered and evaporated to dryness under vacuum. Thus 4.7 g of concentrated liquid extract was obtained. The extract was subjected to high performance liquid chromatography (HPLC) with mass spectrometry and photodiode array detection. Several characteristic phenolic constituents of *Zingiber officinale* Roscoe were observed, such as gingerols, gingerdione, shogaols etc.

3 g of the concentrated liquid extract of *Zingiber officinale* Roscoe was mixed with 7 g of cod liver oil containing eicosapentaenoic acid (20:5n3) and docosahexaenoic acid (22:6n3). Thus a homogeneous mixture was obtained suitable for encapsulation in soft gelatine capsules.

Example 2

A cosmetic composition according to the invention was prepared according to the following recipe:

Cod liver oil, IDA A/S, Denmark 20.0%

Hydrogenated rapeseed oil, Cremeol PS-6, Aarhus Olie. Denmark 10.0%

Sodium stearoyl lactylate, Danisco Ingredients, Denmark 5.0%

Sorbitan monostearate, Danisco Ingredients, Denmark 3.0%

Super Critical ($CO_2$) Extract of *Zingiber officinale* Roscoe 2.5%

Glyceryl monostearate, Danisco Ingredients, Denmark 2.0%

Methyl paraben, Unichem, Denmark 0.3%

Water, purified 100%

Example 3

In a small preliminary clinical investigation two persons administered an oral preparation according to the invention. The preparation comprised a soft gelatine capsule containing:

750 mg of a mixed fish oil derived from herring, salmon, sardine and sinker containing 18% eicosapentaenoic acid (20:5n3) and 12% docosahexaenoic acid (22:6n3).

133 ma extract of *Zingiber officinale* Roscoe.

One patient (male) was 72 years old and had suffered from painful osteoarthritis of the right hand for four years. The patient had in long periods been treated with non-steroidal-antiinflammatory drugs, but had given up the treatment because of unpleasant gastrointestinal adverse effects. The capsule according to the invention was administered twice daily and after four weeks a marked analgesic effect was observed and a significantly better quality of fife was obtained. This level of efficacy was maintained for three months. No adverse effects were observed.

The other patient (female) was 56 years old and had suffered from osteoarthritis of the knee for three years. The patient was treated periodically with non-steroidal-antiinflammatory drugs, but did not obtain a sufficient analgesic effect with this class of drugs. The capsule according to the invention was administered twice daily and after three weeks a marked analgesic effect was observed and this effect gradually improved during two months of treatment. After three months of treatment the same high level of efficacy was maintained with a significant improvement of quality of life. No adverse effects were observed.

What is claimed is:

1. A pharmaceutical, a dietary supplement or a cosmetic composition, comprising:

a) eicosapentaenoic acid (20:5n3) and/or docosahexaenoic acid (22:6n3), b) *Zingiber officinale* Roscoe or parts thereof or an extract or component thereof, and c) a pharmaceutically and/or cosmetically acceptable vehicle.

2. A pharmaceutical, a dietary supplement or a cosmetic composition according to claim 1, wherein the component of *Zingiber officinale* Roscoe is selected from the group consisting of 2-gingerol, 4-gingerol, 6-gingerol, 8-gingerol, 10-gingerol, 12-gingerol, 14-gingerol, 2-shogaol, 4-shogaol, 6-shogaol, 8-shogaol, 10-shogaol, 12-shogaol, 14-shogaol, zingerone, 6-gingerdiol, gingerdione, gingerenones, isogingerenones, zingiberene, bisabolene, ar-curcumene, β-sesquiphelandrene, sesquithujene, β-bisabolone, (E)-α-farnesene, zingiberol, zingiberenol, cis-sesquisabinene hydrate, cis-sesquiphellandrol, trans-sesquiphellandrol and β-phellandrene.

3. A pharmaceutical, a dietary supplement or a cosmetic composition according to claim 1, wherein eicosapentaenoic acid (20:5n3) and/or docosahexaenoic acid (22:6n3) is in the form of an ester or glyceride.

* * * * *